United States Patent [19]

Peterson

[11] Patent Number: 5,629,427

[45] Date of Patent: May 13, 1997

[54] 2,7-DIAMINOMITOSENE ANALOGUES

[76] Inventor: Dwight M. Peterson, 354 Compton Rd., Wyoming, Ohio 45215

[21] Appl. No.: 111,771

[22] Filed: Aug. 26, 1993

[51] Int. Cl.$^6$ .................................................. C07D 487/14
[52] U.S. Cl. ...................... 546/276.7; 548/422; 548/428
[58] Field of Search ............................ 514/411, 19, 27; 548/428, 422; 546/276.7

[56] References Cited

U.S. PATENT DOCUMENTS

| | | | |
|---|---|---|---|
| 3,429,894 | 2/1969 | Matsui et al. | 260/326.3 |
| 4,866,180 | 9/1989 | Vyas et al. | 548/422 |
| 5,103,018 | 4/1992 | Motomichi et al. | 548/422 |

OTHER PUBLICATIONS

Webb et al., J. Am. Chem. Soc. 84, 3185 (1962).
Peterson, D.M. Diss–Abstr–Int–B, 48,2331, (1987).
M. Tomasz & R. Lipman Biochemistry 20, 5056 (1981).
Iynegar et al., J. Med. Chem. 33,253 (1990).
D.M. Peterson & J. Fisher, Biochemistry 25, 4077 (1986).
Han et al., J. Org. Chem. 57, 1799 (1992).
Maliepaard et. al., Anti–Cancer Drug Design, 57, 1799 (1992).
Zervas et. al., J. Am. Chem. Soc. 85, 3660 (1963).

*Primary Examiner*—Johann Richter
*Assistant Examiner*—John Peabody

[57] ABSTRACT

The present invention relates to analogues of 2,7-diaminomitosene, a mitomycin C metabolite, useful as antitumor, antimicrobial and/or antiviral agents. These analogues involve functionalization of the N-2 nitrogen with organic groups.

1 Claim, No Drawings

2,7-DIAMINOMITOSENE ANALOGUES

BACKGROUND AND GENERAL DESCRIPTION OF THE INVENTION

Nomenclature

The present invention provides composition of matter for novel mitosene analogues funtionalized at the N-2 nitrogen. The term mitosene is an abbreviation of the chemical name 2,3-dihydro-9-hydroxymethyl-6-methyl-1-H-pyrrolo[1,2a]indole-5,8-dione, carbamate (Webb, et. al. J. Am. Chem. Soc. 84, 3185 (1962)). The common name 2,7-diaminomitosene, for example, has amino groups at the 2 and 7 carbon positions of the mitosene structure as follows:

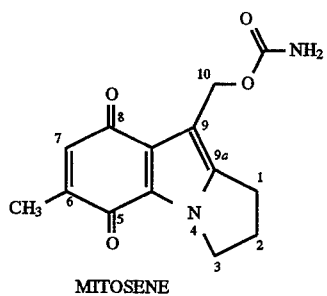

MITOSENE

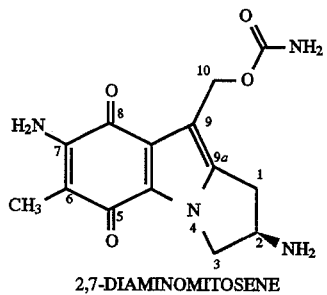

2,7-DIAMINOMITOSENE

General Description of the Invention

Rationale for designing compounds of the present invention is an extension of the finding that the mitomycin C reductive activation product 2,7-diaminomitosene forms noncovalent bonds with deoxyribonucleic acid (DNA) (D. M. Peterson, Diss-Abstr-Int-B. 48, 2331 (1987)). The ideas of the actual conception were to create 2,7-diaminomitosene analogues which have the general structure:

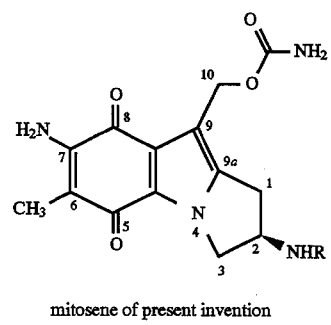

mitosene of present invention and are:

A) are prodrugs that release the cytotoxic 2,7-diaminomitosene, and/or

B) target release of the prodrug by glutathione cleavage of a disulfide bond or aminosulfenyl bond, or C) target release of the prodrug through hydrolysis of an amide, ester or thiolester, or D) take advantage of selective uptake of the mitosene analogue or prodrug through a polyamine, peptide, oligosaccharide or nucleotide transport system, or E) have a functional group that enhances the binding of the agent to DNA such as an oligonuclotide, polypeptide, oligosaccharide or polyamine, or F) have a functional group such as ethanethiol which could produce an additional toxic species (ethylene sulfide) upon prodrug activation by glutathione.

Since mechanisms of action are difficult to prove, utility of these compounds is based on their own empirical antitumor, antimicrobial and/or antiviral activity and not on whether or not the agents act by these particular mechanisms.

Advantages of the Present Invention

One advantage of these mitosenes versus mitomycin analogues is reduced general toxicity. Agents currently used to treat cancer like mitomycin C can be limited by their serious toxic side effects. Compounds which deliver 2,7-diaminomitosene without producing the quinone methide (see scheme below)—a potent alkylating species which results from reductive activation of mitomycin C—are expected to be less toxic. Attack by the quinone methide on various biological macromolecules within a cell (e.g. Nu1= an enzyme) can be toxic. Delivering 2,7-diaminomitosene without the requirement of going through the quinone methide intermediate should reduce prodrug toxicity.

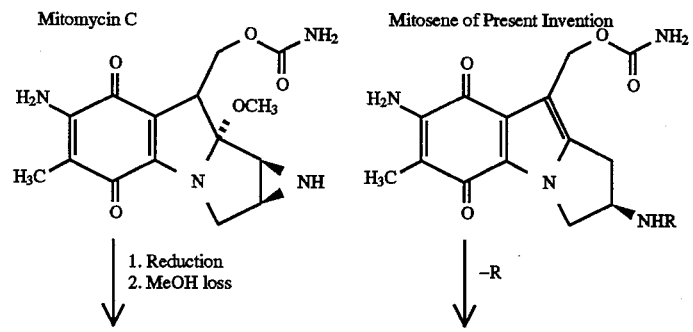

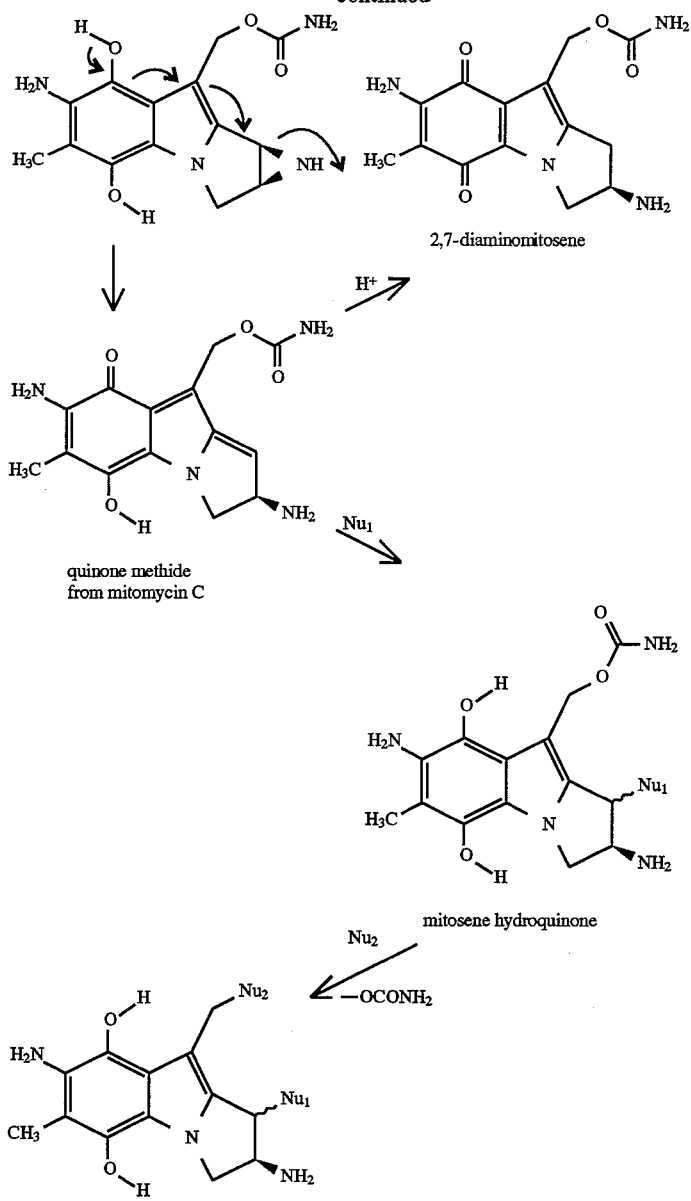

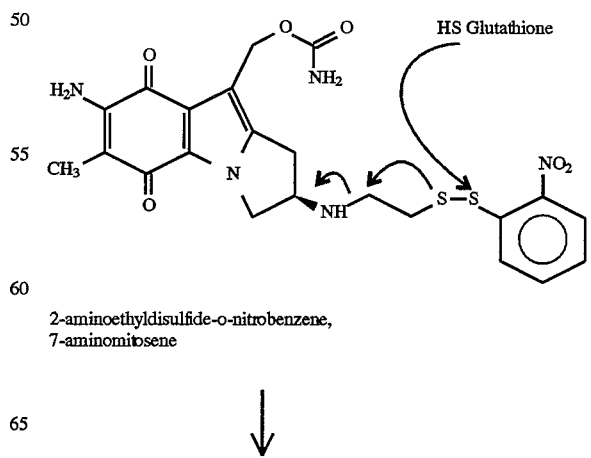

2-aminoethyldisulfide-o-nitrobenzene,
7-aminomitosene

Another potential advantage of the new mitosenes is reduced cell resistance. Current cancer drugs like mitomycin C can be limited by resistance. Drug resistance can occur when high levels of reduced glutathione are present. A proposed mechanism for resistance is nucleophilic trapping of the quinone methide agent (Nu1=glutathione) before 2,7-diaminomitosene and/or crosslinks can form. Properly selecting analogues that would release 2,7-diaminomitosene in the presence of high glutathione levels would avoid the mechanism for mitomycin resistance and actually take advantage of this property of resistant cells for targeted delivery of the agent.

-continued

2 Toxins: 2,7-diaminomitosene and ethylene sulfide (  )

Shown above is the potential to form two toxins which could be employed to adjust toxicity.

Comparison of Present Invention to Mitomycin Analogues

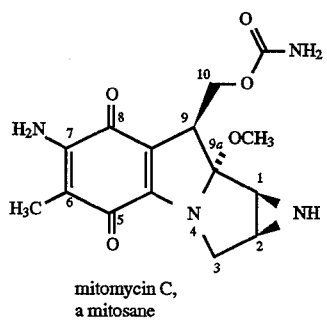

mitomycin C,
a mitosane

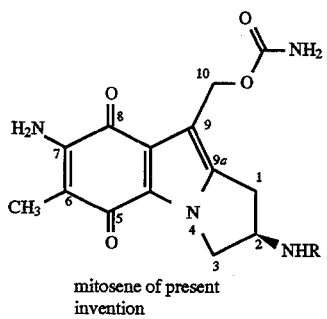

mitosene of present
invention

A clear distinction of the present invention from mitomycin analogues is the presence of a double bond in the 9–9a position for the mitosene. Mitomycin analogues do not possess this double bond and are commonly known in the literature as mitosanes. An even more important distinction is a methylene group at C-1 of the 2,7-diaminomitosene analogues in contrast to an aziridine ring in the mitomycin analogues. Since the mitosene has a methylene, it does not have a suitable leaving group to generate the quinone methide. This inability to form the quinone methide is what gives the mitosene analogues their advantages of reduced toxicity and reduced resistance.

Certain compounds of the present invention contain the general moiety R=$CH_2CH_2SSR'$ (ethyldisulfide groups) which the prior art teaches to attach to an oxygen or nitrogen in the C7 position of the mitosane structure (e.g. U.S. Pat. Nos. 4,866,180 and 5,103,018). In the present invention, the ethyldisulfide groups are attached to the N2 position instead of the N7 position and the resulting composition of matter is a mitosene structure instead of a mitosane structure. The mitosene structure will not form DNA crosslinks and hence is proposed to work by a unique mechanism from the mitosane which is not dependent on the R group.

Comparison of Present Invention to Mitosenes in Prior Art

Since 2,7-diaminomitosene, N-2 R=H, is disclosed in the open literature, it is not a patentable entity (M. Tomasz & R. Lipman, Biochemistry 20, 5056 (1981)). It (2,7-diaminomitosene) has also been shown to possess antimicrobial activity albeit less toxic than mitomycin C under the conditions it was tested (B. Iynegar, R. Dorr, N. Shipp & W. Remers, J. Med. Chem. 33, 253 (1990)). This result, however, could have been influenced by the positively charged amine on 2,7-diaminomitosene which would retard its bioavailability via decreased solubility across a hydrophobic membrane. Attachment of appropriate R groups described in the summary of the invention could increase hydrophobicity by masking the positively charged N-2 amine or facilitate uptake through a cellular transport system and hence increase bioavailability.

Other known 2,7-diaminomitosene derivatives of the general structure are the N-2 R=$COCH_3$ (D. M. Peterson and J. Fisher, Biochemistry 25, 4077 (1986); M. Tomasz & R. Lipman, Biochemistry 20, 5056 (1981)) and N-2 R=$CH_3$, $SO_2CH_3$ or $SO_2C_6H_4pCH_3$ (I. Han, D. J. Russell & H. Kohn, J. Org. Chem. 57, 1799 (1992)). These compounds (R=$COCH_3$, $CH_3$, $SO_2CH_3$, and $SO_2C_6H_4pCH_3$) were produced for chemical studies and are not implicated in their ability to act as antitumor agents. Since these structures are known, however, they are specifically excluded from the mitosene analogue descriptions below.

The general structure is also distinguished from the mitosene analogues which do not possess an amino group at N-2, and/or have an oxygen attached to the analogous C-1 position (M. Maliepaard, et. al., Anti-Cancer Drug Design, 7, 415–425 (1992) and U.S. Pat. No. 3,429,894 "Acetylated Mitosenes"). Moreover, these structures do not have the essential embodiment of a methylene group at C-1 which prevents the formation of a quinone methide.

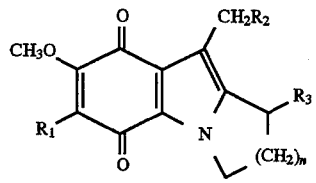

M. Maliepaard, et. al.

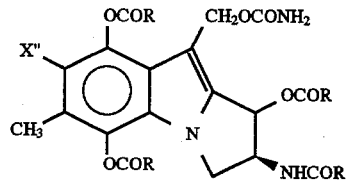

U.S. Pat. No. 3,429,894

DETAILED DESCRIPTION OF THE INVENTION

Appropriate Choice of R Group

The present invention relates to N-2 functionalized analogues of 2,7-diaminomitosene of the general structure above wherein R is not H, $COCH_3$, $CH_3$, $SO_2CH_3$, or $SO_2C_6H_4pCH_3$ but is appropriately chosen from:

A straight or branched alkylene group and/or aromatic group of 1–30 carbons.

A straight or branched alkylene group of 1–30 carbons, which contains 1–20 heteroatoms (e.g. O, N, P or S).

A polyamine with 2–10 amines containing at least 2 carbon atoms but less than 30. Substitutions of amines can be done with other heteroatoms (e.g. O or S). Compounds of specific mention are those structures which have putrescine, spermine or spermidine attached directly to the mitosene (i.e. 2putrescine, 7-aminomitosene; 2-spermidine,7aminomitosene 2-spermidine,7-aminomitosene). Linkers containing 1–30 carbon atoms and 0–10 heteroatoms can also be used to attach the polyamine to N-2 (e.g. 2-aminocarbonyl-spermine, 7-aminomitosene).

An amino acid, or peptide with 2–30 aminoacids, attached directly through an amide bond to N-2 (e.g. 2aminoarginine, 7-aminomitosene, or 2-aminolysine, 7aminomitosene). An amino acid, or peptide with 2–30 aminoacids, attached to N-2 through a linker which contains 0–30 carbons and 1–10 heteroatoms (e.g. N, O, or S). In these compounds the amino acid/peptide is attached to the linker by an aminoacid's carbonyl, amino or functional group (e.g. 2-amino-ethanethiol-arginine, 7-aminomitosene which attaches the ethanethiol linker to the carbonyl group of the amino acid via a thioester bond).

A nucleoside, nucleotide or oligonucleotide with 2–30 nucleotides. This group can be attached to N-2 through a phosphoamide bond, through a C—N bond with C5' of a nucleotide ribose (or deoxyribose), a sulfenylbond with a C5' thioribose (or deoxyribose), or through a linker described for the aminoacid analogues.

An oligosaccharide consisting of 1–30 sugar moieties attached through the anomeric carbon to N2 of the mitosene or through a linker (described above for the peptides) to any of the heteroatoms on the oligosaccharide, or An analogue which is functionalized with a known amino acid protecting group (e.g. o-nitrophenylsulfenyl chloride or 2-nitrobenzyl chloroformate).

A metabolite or catabolite from the fatty acid, citric acid cycle, urea or nucleotide pathways. In the case of compounds containing several functional groups like citrulline, the compound could be be attached via a carbamate, amide, linker or other suitable means of bonding to an amine.

A heteroatom containing branched or straight chained alkylene group of 0–10 carbons. In the case of zero carbons, the heteroatom, such as sulfur, is attached directly to the N-2 amino group. These compounds can be esterified with a carbonyl compound, be attached to an organic compound through a disulfide bond or attached directly to an alkyl, alkylene, or aromatic group. Specific examples of mention are 2-aminosulfenylphenyl-(ortho or para) $NO_2$, 7aminomitosene and 2-aminoethyldisulfidebenzene(ortho or para)$NO_2$, 7-aminomitosene and 2-aminoethylthiobenzoyl, 7-aminomitosene). Replacement of the the nitrophenyl group can be done with an alkyl group or other organic functional group. Glutathione would be one possible functional group.

A compound where N2 forms an azo, aziridino or hydrazine bond with an organic amine.

A compound where N2 is replaced with another heteroatom.

Enablement, Best Mode and Forseeable Variations

Forseeable variations at C-7, C-6 and/or C-10 which are known for mitosane analogues are also expected to be possible for the 2,7-diaminomitosene analogues.

Some specific examples of compounds within the described invention are shown below with their common mitosene names for clarification. This list is not intended to be comprehensive but comprises the envisioned best mode of practice.

Chemistry for modifying primary amines is well known in the art. The present invention relates to attaching functional groups to the primary amine at N2 on 2,7-diaminomitosene using appropriately modified procedures. It is forseeable that improvements to these current techniques will continue to be made, making it possible to produce the mitosene compounds in greater yield although high yield is not considered to be a necessary embodiment for this composition of matter invention.

There are two important considerations which must be taken into account when modifying the literature procedures of primary amines to 2,7-diaminomitosene which may be necessary to improve yields. First, the possibility of modifying N7 exists in addition to the desired N2 modification. The N2 position is the most reactive due to the electron withdrawing effects of the quinone ring on the N7 amine and it should be possible to create conditions which enhance the selectivity (e.g. solvent, order and rate of addition, temperature, stoichiometry of the reagents, etc.) without undue experimentation. For example, formation of amides on 2,7-diaminomitosene with acetic anhydride results in substantially quantitative modification at N2 (D. M. Peterson & J. Fisher, Biochemistry 25, 4077 (1986)). Should the N7 position also react, however, the multifunctionalized compound would be a forseeable modification also having the desired utility within the scope of the invention.

Second, mild conditions are desired when adapting literature procedures of amine reactions due to the lability of certain portions of the mitosene compound—especially the carbamate. If the carbamate is removed in the modification of N2, it is reasonable to assume that standard procedures for adding a carbamate group could be employed to help increase yield. The decarbamoyl mitosene, however, is also considered to be covered under the scope of the present invention since the carbamate is a desired but not necessary feature of the compounds. Should the C10 oxygen of the decarbamoyl mitosene also react with the functionalizing agent used to react with N2, the resulting compound with R attached at C-10 decarbamoyl O and N2 would be a forseeable variation which would retain utility.

As an intermediate starting material, 2,7-diaminomitosene can be prepared from a variety of literature procedures where mitomycin C is reduced under slightly acidic conditions (e.g. M. Tomasz & R. Lipman, Biochemistry, 20, 5056 (1981)).

It is forseeable that one well trained in the art could produce the 2,7-diaminomitosene using organic synthesis by appropriately adapting the references contained in Maliepaard et. al. and other mitosene synthetic procedures and thus avoid the need for mitomycin C as a starting material. The R-stereochemistry at C-2 is potentially achievable using serine as a reactant starting material. Mitosene carbons C1 through C3 are added to an indole after OH—>Cl and $CO_2H$—>CHO conversions on serine. The CHO group is attached to indole nitrogen via schiff base formation and $NaBH_3CN$ reduction. The alternative S-stereochemistry is a forseeable variation which would also have activity.

EXAMPLE

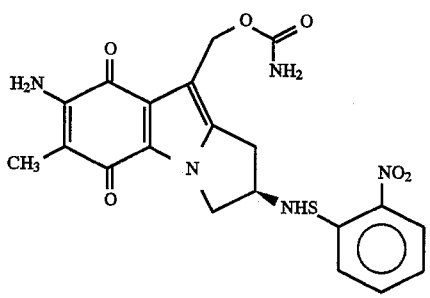

2-aminosulfenyl-o-nitrobenzene,
7-aminomitosene

For the title compound, o-nitrophenysulfenylchloride (oNPSCl) is added using the General procedures for protection of amino acids (e.g. Zervas et. al., J. Am. Chem. Soc. 85, 3660 (1963)). Generally, approximately one equivalent of o-nitrophenylsulfenylchloride is dissolved in THF and added to a mitosene solution in THF and 2N NaOH.

The compound of interest is extracted with $CH_2Cl_2$ and is purified on silica Gel using 5:1 $CH_2Cl_2$:EtOAc. High purity is verified by reverse phase C-18 HPLC using an isocratic eluting system of 60:40 MeOH:0.01M $KH_2PO_4$, pH 6.5 buffer.

NMR ($d_6$-DMSO, 300 MHz) δ8.27 (d, 1H, J=8 Hz, NPS-H), 7.8 (pseudo dd, 2H, J=8,8 Hz, NPS-H), 7.39 (pseudo t, 1H, J=7, 8 Hz, NPS-H), 6.52 (broad s, 4, C7-$NH_2$, C10-OCO$NH_2$), 5.51 (s, 1H, N2-H), 4.98 (dd, 2H, J=12, 17 Hz, C10-$H_2$), 4.16–4.23 (m, 3H, C2-H & C3-$H_2$), 3.03 (dd, 1H, C1-H, J=6, 17 Hz), 2.86 (apparent d, 1H, C1-H, J=16 Hz), 1.71 (s, 3H, C6-$CH_3$).

EXAMPLE

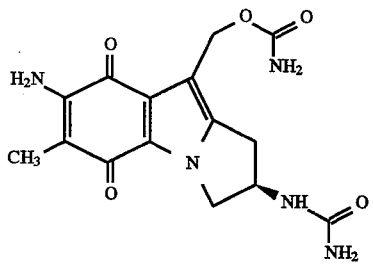

2-aminocarbamate-7-aminomitosene

The title compound can be synthesized with standard carbamate producing reagents. A common reaction to form carbamates is reaction of an amine with sodium cyanate (NaOCN) in an acetic acid:water solution.

EXAMPLE

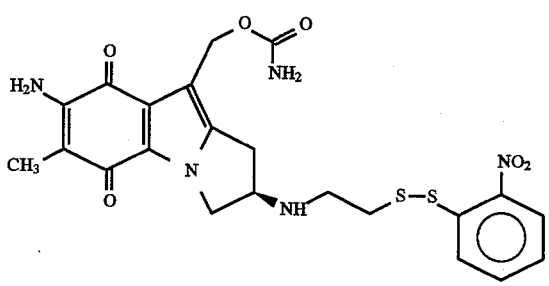

2-aminoethyldisulfide-o-nitrobenzene,
7-aminomitosene 2,7-diaminomitosene can potentially be modified with an in situ mixture of oNPSCl and ethylene sulfide. Typically, the oNPSCl and ethylene sulfide are mixed just prior to addition to 2,7-diaminomitosene.

While there is not an appropriate indication of this chemistry in the literature, the possible mechanism of this reaction is shown below which seems reasonable to assume will work when the appropriate conditions to reduce ethylene sulfide polymerization are worked out.

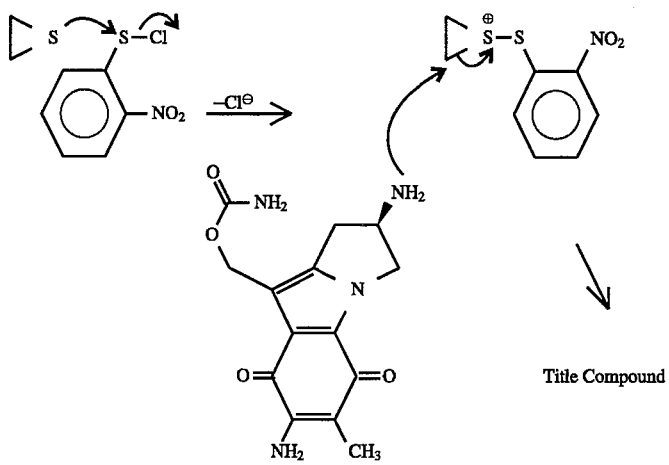

If this reaction turns out to require undo experimentation, there are many other reactions which are possible to make the title compound and are too numerous to efficiently list here.

EXAMPLE

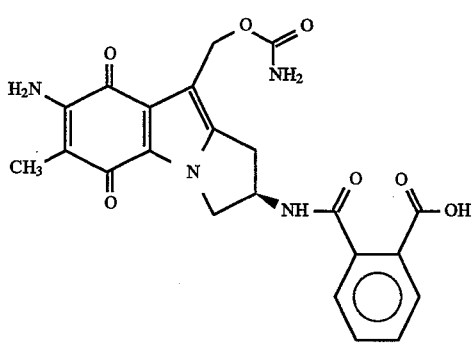

2-aminophthalate,7-aminomitosene

Amides such as this compound can be obtained by reacting a pyridine solution of 2,7-diaminomitosene with the appropriate anhydride or acid chloride.

EXAMPLE

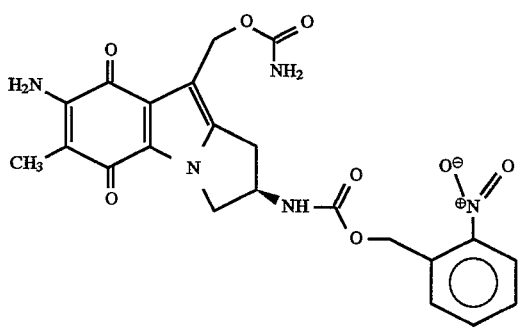

2-amino[[(2-nitrobenzyl)oxy]carbonyl],7-aminomitosene

The 2,7-diaminomitosene starting material can be modified by 2-nitrobenzyl chloroformate, a known amino acid protecting group. Since UV light can be used to remove this protecting group, targeted release of 2,7-diaminomitosene could be achieved using a light energy source (e.g. lamp or lazer) directed at the area of existing or excised tumor tissue.

EXAMPLE

Peptide/Amino acid analogues

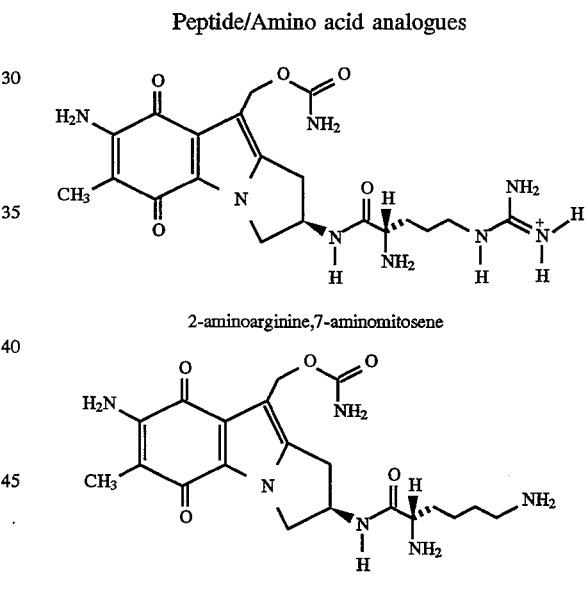

2-aminoarginine,7-aminomitosene 2-aminolysine,7-aminomitosene

The N2 amine position is modified using standard peptide synthesis methodologies which are well known in the art. A mild protecting group strategy is preferable as the 2,7aminomitosene moiety can be sensitive to strong acids, bases and reducing agents. The oNPSCl and DTS protecting groups are suggested because they can be removed with sulfhydryl reagents.

The protected amino acids (e.g. oNPS-arginine, oNPS-lysine or any amino acid with a suitable protecting group) are coupled to 2,7-diaminomitosene using dicyclohexylcarbodiimide (DCC). N-hydroxylsuccinimide is routinely used to help the condensation reaction. The oNPS protecting group is removed with a sulfhydryl reagent such as β-mercaptoethanol.

EXAMPLE polyamine adducts

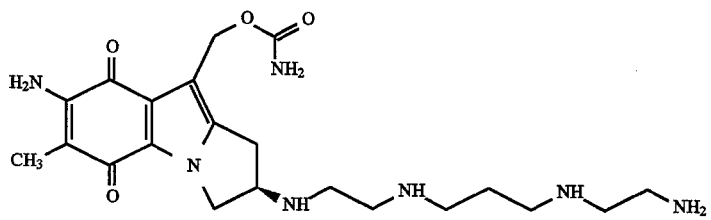

2-spermine,7-aminomitosene

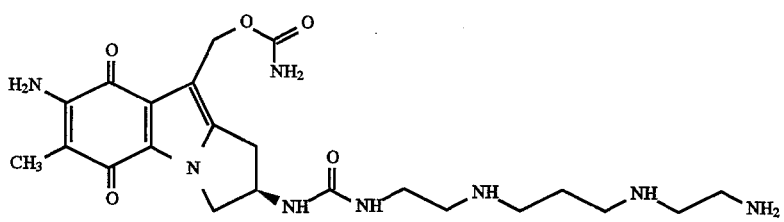

2-aminocarbonylspermine,7-aminomitosene

A polyamine such as spermine can be coupled to 2,7-diaminomitosene using carbodiimidazole via a carbonyl linker or by direct displacement of a triazine formed with one of the spermine nitrogens by the N-2 mitosene nitrogen. To increase yields, a suitable protecting group, such as trifluoroacetic anhydride (or chloride), can be used to block one of spermine's primary nitrogens prior to the reaction. Removal of the trifluoracetic acid protecting group can be done with methanolic ammonia.

Standard oligonucleotide synthesis methodologies which are well known in the art can be used to react the 2-amino group or 2 aminoethanethiol group with an activated phosphate group. Mild protection strategies should be employed to avoid degradation of the mitosene moiety during deprotection.

EXAMPLE nucleotide adducts

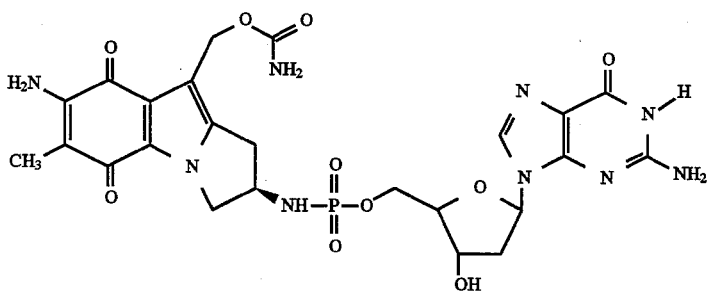

2-aminomonophosphateguanine,7-aminomitosene

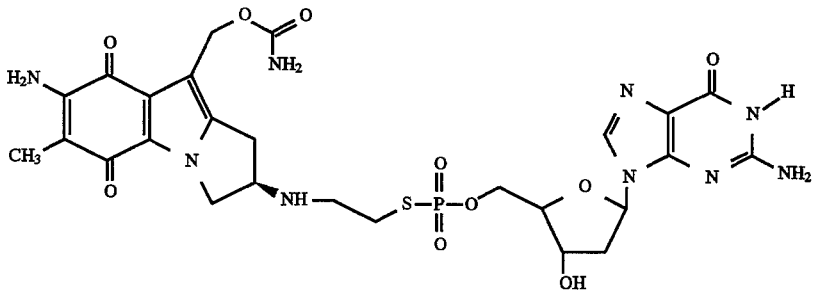

2-aminoethylthiolmonophosphateguanine,7-aminomitosene

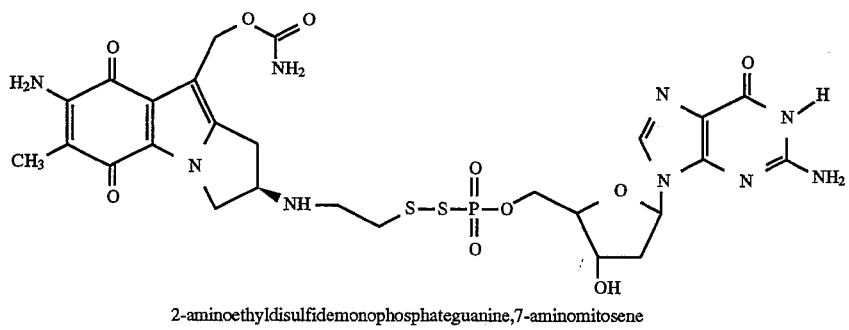

2-aminoethyldisulfidemonophosphateguanine,7-aminomitosene

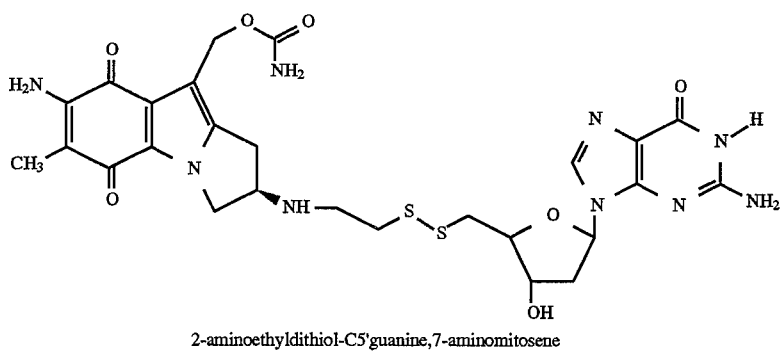

2-aminoethyldithiol-C5'guanine,7-aminomitosene

Compounds such as these can be obtained by disulfide exchange resulting in displacement of a labile thiol such as o-NPS from 2-aminoethyldissulfide-o-nitrobenzene by 5' thiol or 5' thiophosphate nucleotides, respectively.

EXAMPLE
Diazo and hydrazine bond linkages

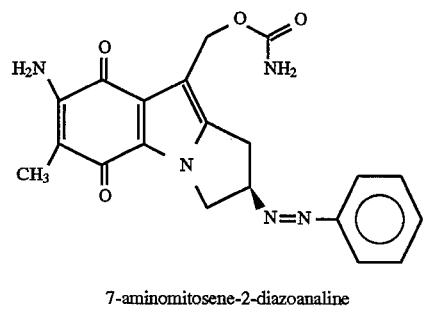

7-aminomitosene-2-diazoanaline

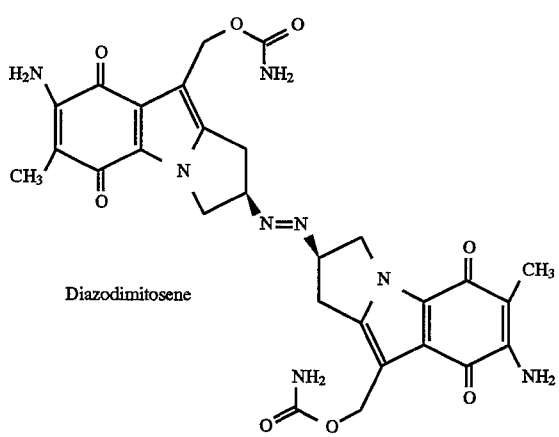

Diazodimitosene

Diazo derivatives of 2,7-diaminomitosene can be made by reaction with the appropriate nitroso compound formed by reacting a primary amine with $K_2S_2O_8$ (potassium persulfate). Hydrazine species can be formed by mild reduction of the diazo compounds although a significant degradation of the 2,7-diaminomitosene compound could occur. Other suitable methods of preparing hydrazines are well known in the art.

EXAMPLE

R groups with more than one way of attachment to an amine

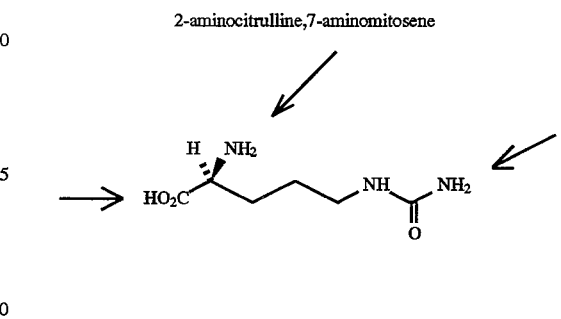

2-aminocitrulline,7-aminomitosene

Multifunctional R groups such as citrulline can be attached in a variety of ways. In general, the following funtional groups can be attached to the N2 primary amine. The suggested generalized procedures can be replaced with other reactions well known in the art.

| Functional Group | Attachment |
|---|---|
| Carboxylic acid | Amide bond<br>Use anhydride or acyl chloride in pyridine or condesation with appropriate agent such as DCC. |
| Amine | Carbonyl or other suitable linker<br>Use carbodiimidazole or other reagent for desired linker.<br>Diazo or hydrazine<br>Preform nitroso amine with $K_2S_2O_8$ and react with N2. Reduce diazo to form hydrazine.<br>Replace an amine in structure with N2 (i.e. minus one nitrogen-- amine of structure is attached directly to the mitosene backbone).<br>Form triazine from amine and displace with N2. |
| Thiol | Sulfenyl bond<br>Use appropriate sulfenyl chloride<br>Disulfide bond with thiol linker<br>Disulfide exchange of a mitosene disulfide such as 2-aminoethyldisulfide-o-nitrobenzene. |
| Carbamate | Replace a carmamate amine with N2 as decribed for amine (terminal $NH_2$ of carbamate is attached directly to the mitosene backbone)<br>React N2 with appropriate cyanate reagent. |
| Sulfate | Sulfonamide bond<br>React N2 with appropriate sulfonyl chloride. |
| Phosphate | Phosphoamide bond<br>React N2 with appropriate activated phophate.<br>Choose an appropriate linker |
| Alcohol | Choose an appropriate linker (e.g. a dicarboxylic acid forming an amide bond to the mitosene and ester bond to the alcohol).<br>One option: React alcohol with cyclic anhydride and condense with N2 using DCC. |

I claim:

1. A composition of matter of the general structure I

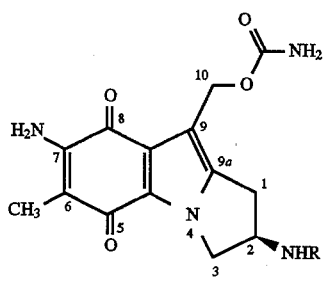

General Structure I where R is:

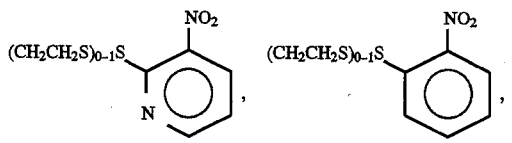

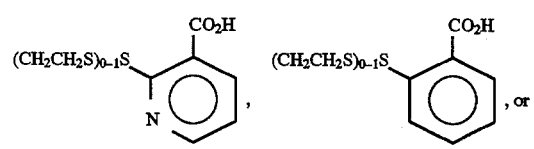

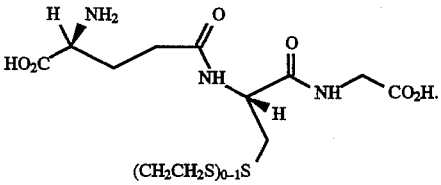

\* \* \* \* \*